United States Patent [19]

Kurbatov et al.

[11] Patent Number: 5,684,851
[45] Date of Patent: Nov. 4, 1997

[54] IMAGING METHOD AND APPARATUS USING PENETRATING RADIATION TO OBTAIN AN OBJECT PROJECTION

[75] Inventors: Alexey V. Kurbatov, Moscow, Russian Federation; Pavel I. Lazarey, Menlo Park, Calif.

[73] Assignee: Quanta Vision, Inc., San Mateo County, Calif.

[21] Appl. No.: 564,014

[22] Filed: Nov. 29, 1995

[30] Foreign Application Priority Data

Nov. 30, 1994 [RU] Russian Federation ............ 94042608

[51] Int. Cl.⁶ .................................................. G01N 23/20
[52] U.S. Cl. ............................. 378/87; 378/149; 378/154
[58] Field of Search ............................ 378/62, 87, 98.2, 378/98.4, 145, 147, 149, 154, 158, 159

[56] References Cited

U.S. PATENT DOCUMENTS

| | | | |
|---|---|---|---|
| 4,549,307 | 10/1985 | Macovski | 378/147 X |
| 4,651,002 | 3/1987 | Anno | 378/98.4 X |
| 4,656,650 | 4/1987 | Kikuchi et al. | 378/98.4 X |
| 4,677,681 | 6/1987 | Klausz | 378/98.4 X |
| 4,688,242 | 8/1987 | Ema | 378/62 X |
| 4,727,562 | 2/1988 | Belanger | 378/145 X |
| 4,741,009 | 4/1988 | Yamagata et al. | 378/98.4 |
| 4,761,802 | 8/1988 | Kiri | 378/98.4 |
| 5,319,694 | 6/1994 | Ingal et al. | |
| 5,533,088 | 7/1996 | Fivez | 378/98.2 X |

FOREIGN PATENT DOCUMENTS

| | | |
|---|---|---|
| PM0583 | 8/1993 | Australia. |
| PM1519 | 9/1993 | Australia. |
| PM1597 | 10/1993 | Australia. |
| PM4298 | 3/1994 | Australia. |
| WO95/05725 | 2/1995 | WIPO. |

OTHER PUBLICATIONS

Mitrofanov, et al, "Method of Obtaining the Shadow of an Object Internal Structure with the aid of Penetrating Radiation", *NAOUKA* Pub., 1982, pp. 221–222.

L. M. Soroko, "Gilbert's Optics," Nauker, 1981, pp. 34–37, 90–93, 126–127, 160–169, and 236–239.

Vinogradov et al., "Investigation of a Steering Mirror for the Soft X–Ray Region," Nuclear Instruments and Methods in Physics Research, 1987, pp. 11–12.

Vinogradov et al., "Turning a Ray of Soft X–Ray Radiation by Means of a Spherical Surface," (Russian publication, 13 Nov. 1985) pp. 594–596.

*Primary Examiner*—David P. Porta
*Attorney, Agent, or Firm*—Skjerven, Morrill, MacPherson Franklin & Friel; Thomas S. MacDonald; David T. Millers

[57] ABSTRACT

An imaging system spatially modulates penetrating radiation that passes through an object under investigation. The modulation introduces spatial irregularities which can be deflected while passing through the object under investigation. The deflection of each irregularity can be identified and is converted into contrast of in a projection of the object. One embodiment of the invention includes: a source of penetrating radiation 1, and a modulator 3 for the creation of spatial irregularities; and a detector 5 for measuring transverse translations of spatial irregularities and converting the measured transverse translations into contrast in a projection 8 of object 4.

20 Claims, 8 Drawing Sheets

IMAGING METHOD AND APPARATUS USING PENETRATING RADIATION TO OBTAIN AN OBJECT PROJECTION

BACKGROUND OF THE INVENTION

Field of the Invention

This invention relates to methods and devices for non-destructive analysis of an object, and more particularly to using penetrating radiation to form a projection of the object.

Description of Related Art

Penetrating radiation has been used to analyze the internal structure of biological objects such as humans and animals and inorganic objects made of materials such as metals, polymers, and ceramics which are opaque to visible light. A common method of analyzing an object's internal structure irradiates the object with a beam of penetrating radiation such as X-rays and detects the radiation that passes through the object. A suitable detector such as film sensitive to the penetrating radiation receives the radiation that passed through the object and forms a picture or projection which indicates a two-dimensional distribution of the radiation intensity. The two-dimensional distribution of intensity arises because the object contains areas that differ in ability to attenuate penetrating radiation.

Such distributions provide little information about the internal structure of objects having low ability to attenuate the penetrating radiation or objects containing areas that differ only slightly in their ability to attenuate the penetrating radiation. Additional information about the internal structure of an object can be obtained by measuring the angular deflection of the penetrating radiation that has passed through the object. The angular deflection provides information mainly about the refractive and scattering characteristics of matter in the object.

K. M. Podurets, V. A. Somenkov, S. Sh. Shilshtein, "Refraction Contrast Radiography", J. of Tech. Physics, v.59, #6, 1989, pp. 115–121 describes a radiographic projection method which uses penetrating radiation such as x-rays, neutron beams, or synchrotron radiation and converts deflection of the radiation that has passed through the object under investigation into the contrast in an object projection. This method uses an apparatus including: a source of penetrating radiation, a collimator to form a radiation flow directed to an object under investigation, a facility to convert the angular deviation of the radiation that passes through the object under investigation into contrast in the projection, and a detector to detect the radiation that has passed through the object undeflected. The collimator contains a monocrystal set in a reflecting position in accordance with Bragg's law, and a diaphragm with a slit to define the radiation beam. The facility intended to convert angular deflection of the radiation into contrast in the object projection also contains a monocrystal set in a reflecting position in accordance with Bragg's law, and collimates the radiation flow. The monocrystals limit the fraction of radiation which is useful in forming the projection because the monocrystals reflect only radiation at wavelength within a narrow spectral band that falls within an angle limited by the width of the reflection curves of monocrystals. As a result, only a small part of the radiation passing through the object reaches a detector, and a long exposure is required to provide a projection with suitable contrast.

SUMMARY OF THE INVENTION

An imaging system in accordance with an embodiment of the invention overcomes defects of the known systems by spatially modulating penetrating radiation, passing the modulated radiation through an object under investigation, and converting angular deviations of the radiation into contrast in a projection. Measuring the translation of the spatial modulation in a direction transverse to the undeflected radiation flow indicates the angular deviation. Spatial modulation of the penetrating radiation is realized by introducing local darkenings into the flow, while a lateral translation of the spatial modulation caused by the object under investigation is determined by measuring the displacement and distortion of the local darkenings in the direction transverse to the undeflected direction of the penetrating radiation flow. To measure the translation of the local darkenings, the undeviated fraction of radiation flow is intercepted while a non-intercepted part of the radiation flow is registered to evaluate displacements of the darkenings. This provides a dark field projection (or image) that improves ability to detect deflections.

One embodiment of the invention converts the penetrating radiation that has passed through the object under investigation into visible light, and measures darkening displacements in the penetrating radiation by registering changes in the position and shape of the spatial distribution of the visible light. The fraction of the visible light radiation formed by the undeviated part of the penetrating radiation flow is intercepted (blocked). Another embodiment of the invention converts into light only the penetrating radiation deviated while passing through the object under investigation. In both embodiments, light radiation can be processed using optical systems to form an image. Alternatively, a position-sensitive detector can measure the displacement of a darkening.

One embodiment of the invention includes: a source of penetrating radiation, a collimator to form a beam of penetrating radiation directed to the object under investigation, and a mean to convert angular deviations of radiation flow that passes through the object under investigation into the contrast in an object projection. In accordance with this embodiment, the apparatus has a modulator or spatial filter to form transverse spatial irregularities in the penetrating radiation flow; and the means for converting contains a detector for measuring lateral translations of the spatial irregularities. Typically, the detector for measurement of lateral translations of spatial irregularities is a spatial filter containing opaque and transparent areas.

A luminescent screen between the object under investigation and the spatial filter can convert the penetrating radiation into light, and a mask formed on the screen can block light or light formation in prescribed areas. It is desirable to use an optical system between the luminescent screen and transparency to collect the luminescent radiation rays and increase the intensity of the radiation.

The detector for the measurement of lateral translations of the spatial irregularities may include luminescent substances and a screen with areas having different luminescent properties. The detector may also include an optical system for changing the direction of light radiation induced by the penetrating radiation. In particular, an optical system for the collection of luminescent radiation rays contains a "collective" element in the form of an optic raster. The detector for measurement of lateral translations of spatial irregularities may alternatively include a position-sensitive detector.

BRIEF DESCRIPTION OF THE DRAWINGS

Use of the same reference symbols in different figures indicates similar or identical items.

DETAILED DESCRIPTION OF THE PREFERRED EMBODIMENTS

Figure 1:
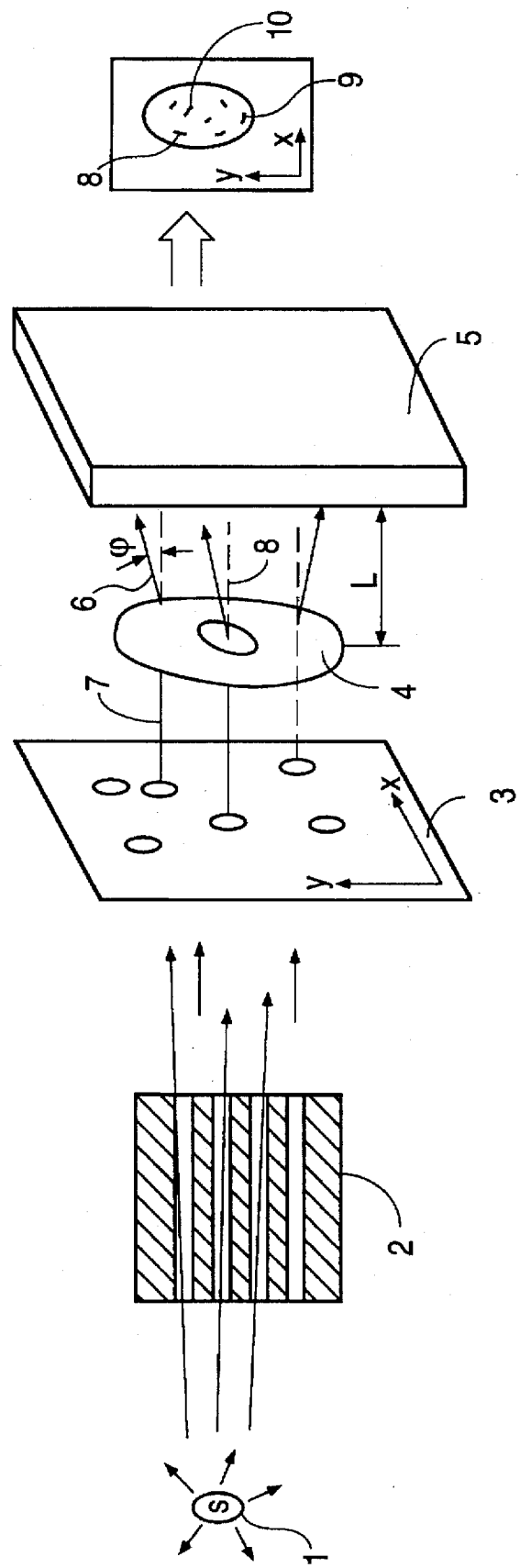
FIG. 1 shows an imaging system which uses penetrating radiation to produce an object projection.

FIG. 1 shows an imaging system in accordance with an embodiment of the invention. In the imaging system, a source of penetrating radiation 1, which may be a roentgen tube, for example, is at some distance from a collimator 2 intended to form a penetrating radiation flow with small divergence. In the path of the collimated flow is a spatial filter 3 which spatially modulates the radiation flow to create irregularities in intensity transverse to the flow direction. An object under investigation 4 is placed directly after spatial filter 3 so that the penetrating radiation flow pierces all of object 4 or its investigated part.

Detector 5 may include film, a position-sensitive detector, or a luminescent screen, which accepts the penetrating radiation that has passed through object 4 and registers or measures the transverse translation (displacement) of the spatial modulation or irregularities in radiation flow. A distance L between object 4 and detector 5 is such that the transverse translations of the flow irregularities due to deviation of radiation flow caused when the radiation flow passes through object 4 are within range that detector 5 is capable of detecting.

While the modulated penetrating radiation passes through object 4, object 4 deflects rays 6 of the radiation so that rays 6 are at an angle φ relative to the direction of rays 7 which are in the direction that the radiation had prior to entering object 4. Deviated rays 6 and undeviated rays 7 that have passed through object 4 carry the modulation formed by spatial filter 3. Detector 5 detects the lateral displacements of intensity unevenesses which spatial filter 3 impressed on the radiation and uses the lateral translations for producing contrast in a projection 8 of object 4. The contrast in projection 8 is displayed as the presence of areas 9 and 10 that differ in brightness or color and indicates areas in object 4 which differ in scattering and/or refractive characteristics.

Figure 2B:
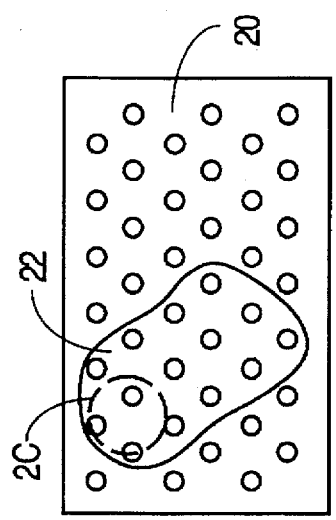
FIG. 2 shows an imaging system which forms a projection indicating deflection of spatial modulation in penetrating radiation.
Figure 2C:
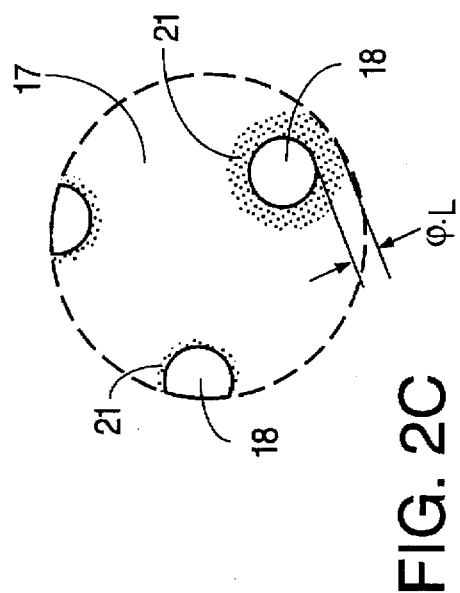
Figure 2A:
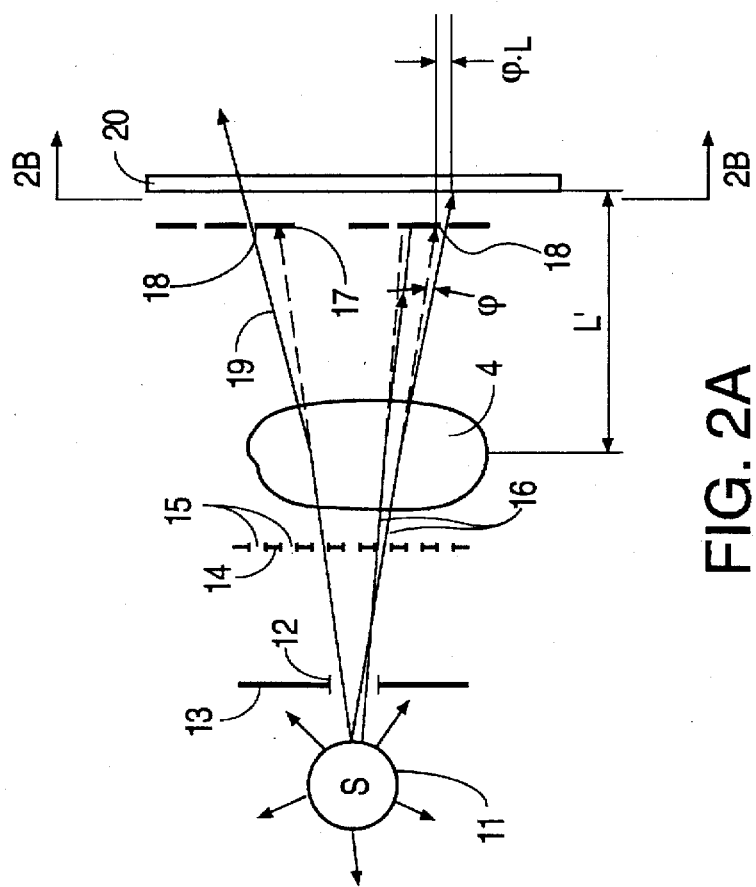

FIG. 2 shows another apparatus in accordance with an embodiment of the invention. In FIG. 2, a source of penetrating radiation 11 illuminates a diaphragm 13 containing an aperture 12 that presets and fixes the effective position and size of source 11. A spatial filter 14 is in the path of the radiation flow that diverges after leaving aperture 12. Spatial filter 14 is a plate made from the material effective at absorbing the radiation from source 11. For example, spatial filter 14 may be made of lead for absorption X-rays. A plurality of apertures 15 in spatial filter 14 transmit modulated, penetrating radiation 16. In one embodiment, apertures 15 are circular. Radiation 16 that passes through apertures 15 is collimated, and edges of apertures 15 prescribe the spatial modulation of the radiation flow. Object under investigation 4 is placed directly behind spatial filter 14 in the path of collimated and modulated radiation flow. A second spatial filter 17 is at some distance from spatial filter 14 along the direction of the collimated and modulated rays 16. Spatial filter 17 has areas 18 which are opaque to the penetrating radiation and are positioned to block undeflected radiation. Distance L from spatial filter 17 to object 4 is such that rays 19, which are deviated from the direction that radiation entered object 4, are translated to a distance which a detector 20 can measure.

Radiation rays 19 that pass through object 4 form a system of spots (darkenings) 21 on spatial filter 17 surface. The darkenings are projections of aperture 12 in diaphragm 13. Opaque areas 18 of spatial filter 17 are located at the places where rays undeviated by object 4 form projections of apertures 15. The remaining parts of spatial filter 17 are made from a material that is penetrable to the radiation. As a result, some of the deviated rays get to penetrable areas of spatial filter 17 and pass through to detector 20. Detector 20 registers the two-dimensional distribution of the radiation flow intensity of radiation passing through spatial filter 17.

The radiation absorption in object 4 and the magnitude of translations of boundaries of spots (darkenings) 21 relative to opaque areas 18 of spatial filter 17 determine the intensity of the radiation registered by detector 20. Accordingly, a non-uniform distribution of translations creates contrast in a projection 22 of object 4. The magnitude of a translation of a spot is the product of an angle of deflection by the distance travelled from object 4 to detector 20. Enlarging distance L increases the translation and can improve contrast in projection 22.

In an exemplary embodiment of the imaging system shown in FIG. 2, source of penetrating radiation 11 is a Roentgen tube with a copper anode and generates characteristic radiation with the wavelength of 1.54 Å. Diaphragm 13 limits radiation flow to a 0.01-mm diameter circular aperture 12. Spatial filter 14 is made from a material such as lead foil that is opaque to X-rays is 1 m from diaphragm 13. A set of circular apertures 15 in spatial filter 14 are 0.01 mm diameter and are 0.05 mm from each other at the vertices of a net of equilateral triangles having sides 0.05 mm in length. Spatial filter 17 is made from an amorphous material transparent to X-rays (quartz, for example) and is 1 meter from spatial filter 14 along the line of radiation flow. The surface of spatial filter 17 is masked with the net of areas 18 (round plates 0.06 mm in diameter) which are opaque to X-rays and located at 0.1 mm distance from each other at the vertices of a net of equilateral triangles.

The shape and location of opaque areas 18 are chosen in so that they completely block X-ray rays from spatial filter 14 that has pass through object 4 undeflected. Projections of apertures 15 of spatial filter 14 can be aligned with areas 18 of spatial filter 17 by replacing detector 20 with a conventional glow-discharge radiation counter and then adjusting the position of spatial filter 14 to minimize the rate of counting of the counter.

The size of projection 22 indicates the size of object 4 because the penetrating radiation propagates linearly with only small deflection in object 4 to create contrast in the projection 22. The correlation between the size of projection 22 and the size of object 4 can be determined simply from the geometry of the imaging system. The size of projection 22 may be changed by converting penetrating radiation into visible light and subsequent optical processing of the light induced by the penetrating radiation.

Figure 3:
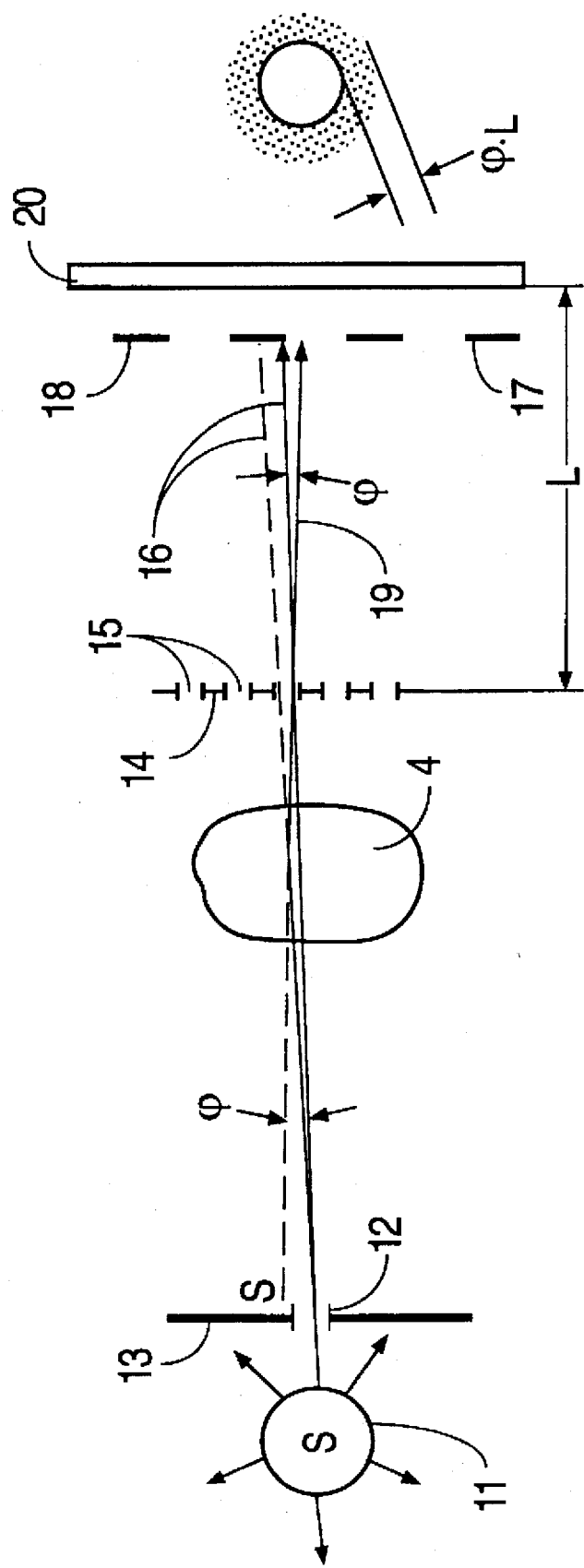
FIG. 3 shows an imaging system where an unmodulated flow of penetrating radiation passes through an object under investigation and then is modulated in the process of measuring a deflections.

FIG. 3 shows an embodiment of an imaging system where object 4 is in front of spatial filter 14. This position of object 4 increases the dose of penetrating radiation on object 4 because parts of the radiation flow which spatial filter 14 blocks and which do not take part in the forming a projection pass through object 4. Filter 18 contains opaque regions positioned to block radiation which passes from diaphragm 13 and spatial filter 14 without being deflected in object 4. Accordingly, only radiation deflected in object 4 passes through spatial filter 18 and reaches detector 20.

Figure 4:
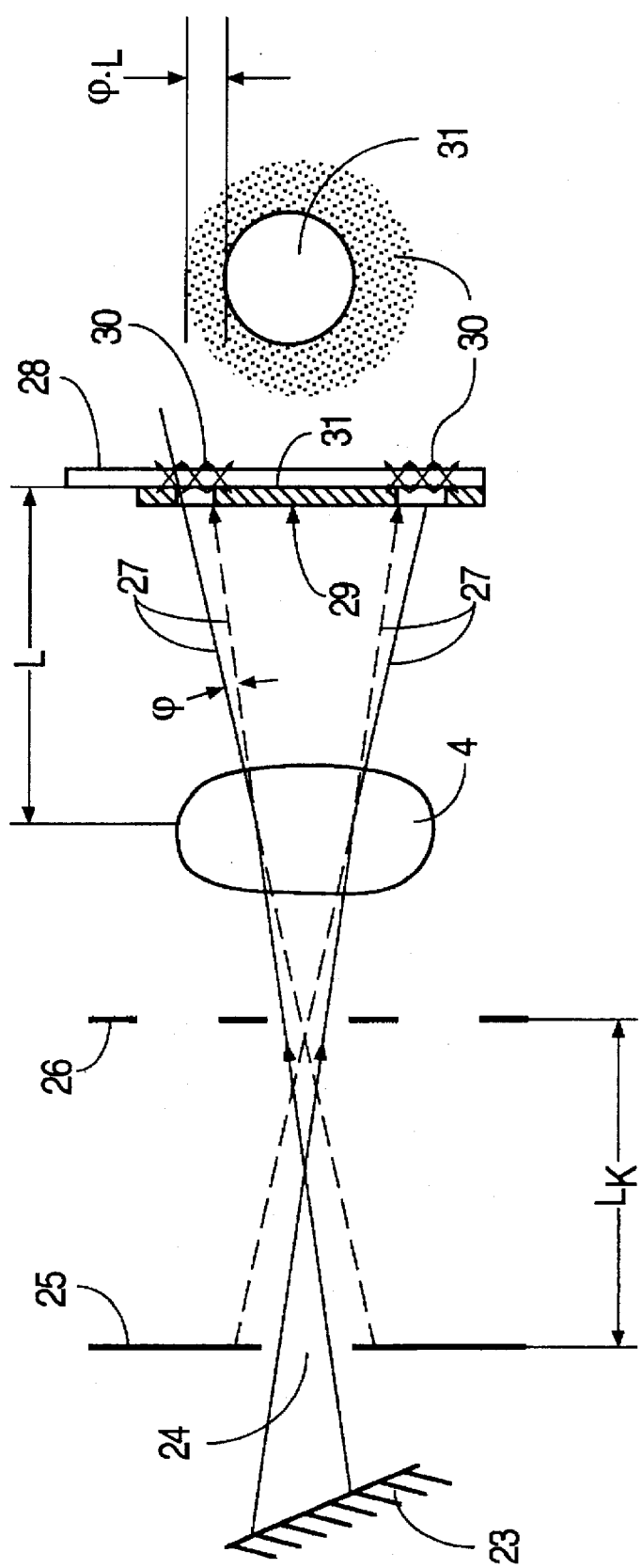
FIG. 4 shows an imaging system which converts penetrating radiation into visible light and measures the boundaries of the light.

FIG. 4 shows an imaging system where a penetrating radiation source (Roentgen tube) 23 is before an aperture 24 in a diaphragm 25. A spatial filter 26 is in the path of penetrating radiation from aperture 24 and acts as a collimator and a modulator. Penetrating radiation flow collimated and modulated by spatial filter 26 passes through object 4, and then rays 27 that passed through object 4 strike luminescent screen 28. A spatial filter 29 located before screen 28 blocks part of the penetrating radiation. An unblocked part of the radiation reaches screen 28 and causes the fluorescent illumination (shown by small arrows) of the screen's luminophore in zones 30. Spatial filter 29 is opaque for the penetrating radiation in areas 31 and blocks mainly the part of the radiation flow which was not deflected in object 4. Deviated rays cause the illumination of luminophores in zones 30 of screen 28. The greater is the magnitude of lateral displacement on screen 28, the greater is the area of luminophore irradiated and the greater is the intensity of the illumination.

Distribution of the illumination intensity over screen 28 may be registered visually, photographed, or input into a computer. A conventional optical system such as a system of lenses and mirrors (not shown) can process the light emitted from screen 28 by projecting the luminescence on a light sensitive detector (not shown). The optical system can also alter the scale of the projection.

Figure 5:
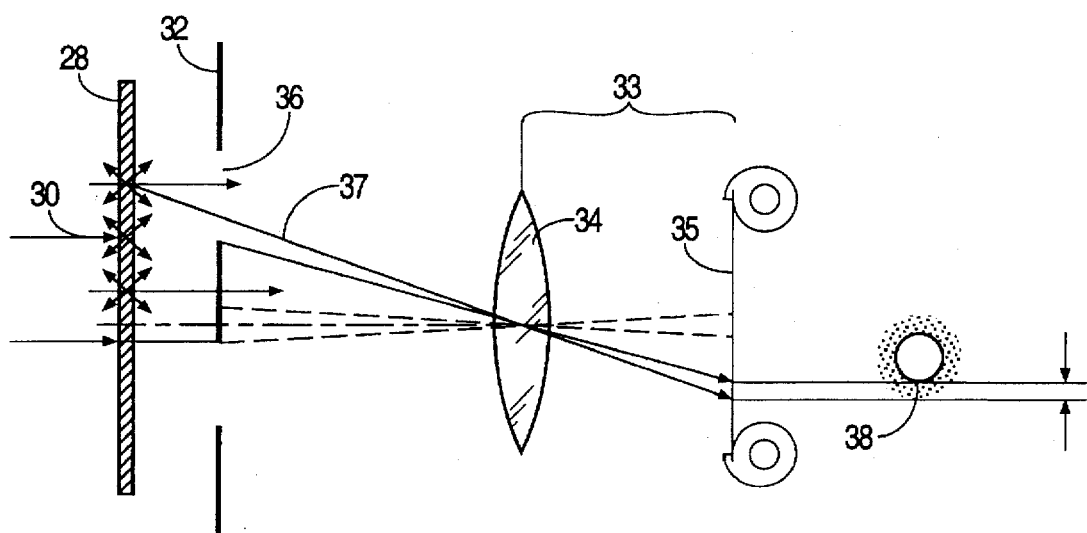
FIGS. 5 and 6 show alternative systems for the measurement of light displacement in the apparatus of FIG. 4.

Measurements of lateral translations of the penetrating radiation beam may be carried out after converting the penetrating radiation into visible light. FIG. 5 shows one example detector 33 which may be added to the imaging system of FIG. 4 to measure lateral translations. In the system of FIG. 5, screen 28 emits a fluorescent luminescence that a spatial filter 32 located behind screen 28 shapes. Detector 33, which is a camera containing an optical system 34 and light sensitive film 35, registers the light radiation that passes through spatial filter 32. Spatial filter 32 has opaque regions and transparent openings 36. The opaque regions of spatial filter 32 fall in the path of the light radiation induced by the undeviated fraction of the penetrating radiation. Accordingly, the fraction of light radiation emitted by each zone 30 of screen 28 that reaches film 35 depends mainly on the magnitude of the lateral translations at screen 28. A greater fraction of light beam passing through masked spatial filter 32 provides greater intensity at film 35.

The distorted light spot produced by an un-blocked part of light flow is shown on FIG. 5 as hatched area 38. A collection of such areas having differing intensity and size forms a picture of the two-dimensional distribution which is correlated with deflection within object 4.

Figure 6:
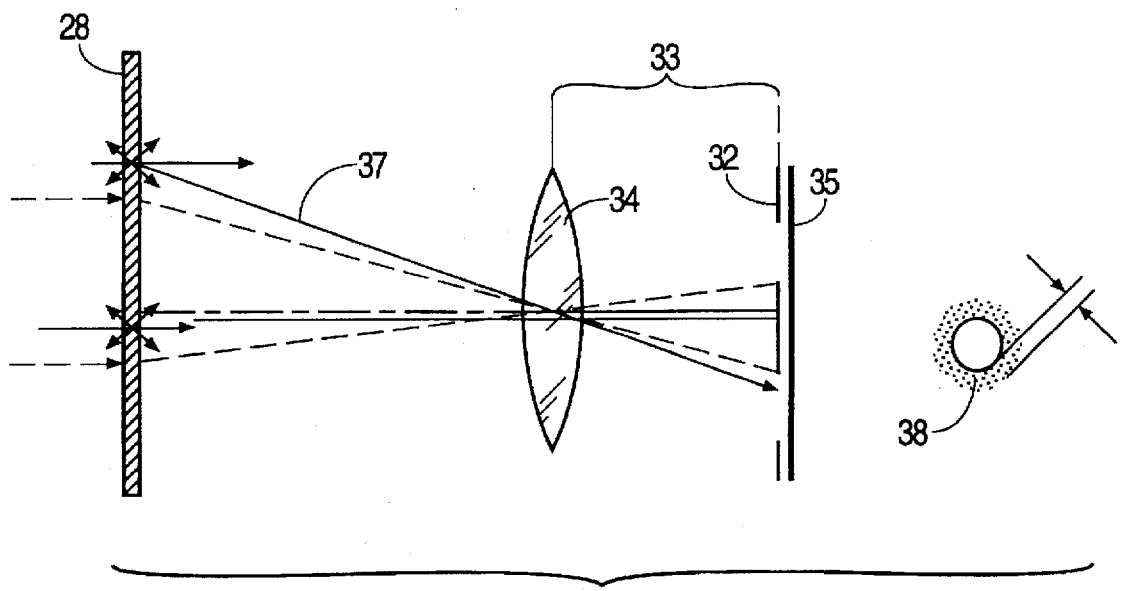

FIG. 6 shows an optical system where spatial filter 32 is between optical system 34 and film 35 rather than before optical system 34 as shown in FIG. 5. In practice, spatial filter 32 placed after optical system 34 is fabricated by a photo method which projects undeflected light spots through optical system 34 onto spatial filter 32 and exposed regions of spatial filter 32 are made opaque. This procedure compensates for the distortions caused by optical system 34. This embodiment of the invention can use light collecting means of any known design (not shown) in optical system 34 to increase the fraction of fluorescent radiation directed to film 35 in detector 33. Said light collecting means can contain a plurality of convergence microlenses focused on the screen 28 surface.

Figure 7:
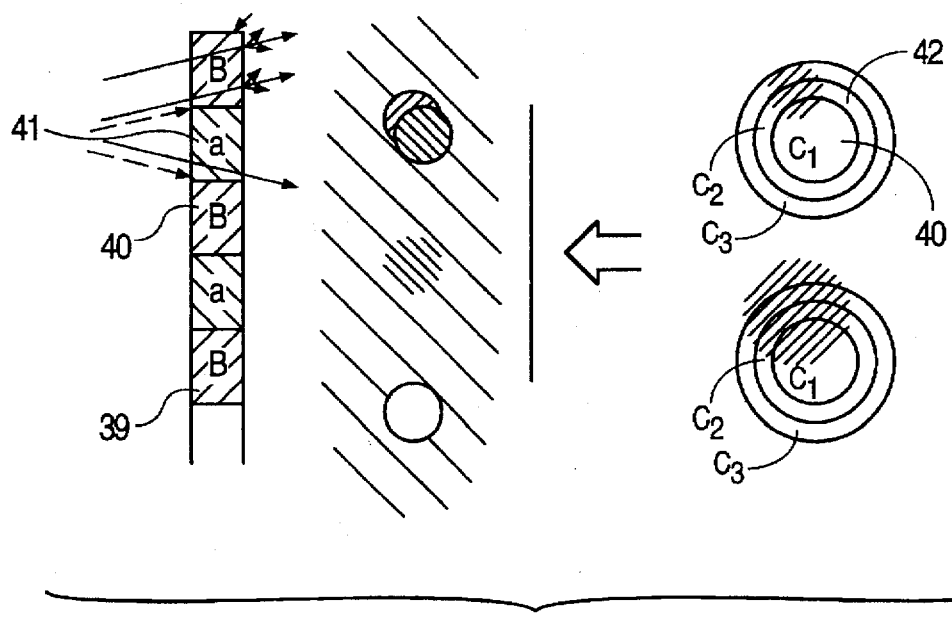
FIG. 7 shows a detector including a screen having an inhomogeneous covering of phosphore for the measurement of translations in penetrating radiation.

In the systems shown in FIGS. 4, 5, and 6, spatial filters 29 and 32 allow measurement of deflected penetrating radiation by blocking the undeflected penetrating radiation and/or blocking fluorescent light that results from the undeflected radiation. FIG. 7 shows a screen 39 that can be used without a spatial filter when measuring deflection of penetrating radiation. Screen 39 has areas 40 and 41 that differ from each other in their fluorescent characteristics such as color, brightness, or polarization of emitted fluorescent radiation. Lateral displacement of the darkening edges in the penetrating radiation falling at screen 39 changes the amount of penetrating radiation striking areas 40 and 41 and changes the fractions of the fluorescent light radiation from each area 40 and 41. A detector sensitive to the alteration of the characteristics of the fluorescent radiation can measure a two-dimensional distribution of the fluorescent characteristic and form a contrast projection of the object under investigation.

In one of the embodiment, areas 40 and 41 on screen 39 contain substances which emit fluorescent radiation of different colors. If the modulated penetrating radiation reaches screen 39, the resulting fluorescent light radiation consist of a combination of different colors that depend on where the penetrating radiation strikes screen 39, and the different colors emitted by areas 40 and 41. Lateral translation of the darkenings changes the proportions of light from areas 40 and 41, and the change in proportions manifests itself in a projection as areas of different color, i.e. a chromatic contrast.

Another variant of the embodiment shown in FIG. 7, has an absolute absence (or a strong attenuation) of any fluorescent properties in certain parts of areas 40 when compared to areas 41 on screen 39. In this variant, screen 39 can be formed by local elimination of luminophore from areas 40 or treating areas 40 to quench the fluorescence. Typically, the areas of weakened fluorescence are in the path of undeviated penetrating radiation so that transverse displacements of the penetrating radiation increase the proportion of the penetrating radiation which strikes fluorescent areas having the stronger fluorescent characteristics (light output). Thus, areas of object 4 which produce greater deviation of radiation beam create the bright areas in a projection. Placing areas of higher fluorescent light output in the path of the undeviated penetrating radiation provides a projection that is the negative in contrast of a projection formed by the embodiment having areas of lower fluorescent light output in the path of the undeviated penetrating radiation.

Figure 8:
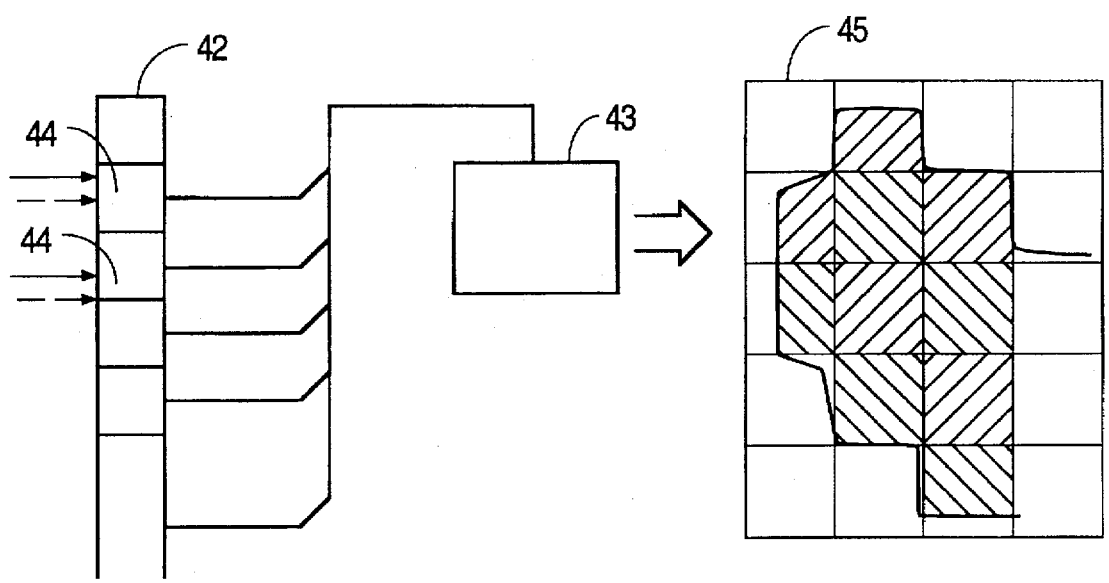
FIG. 8. shows a position-sensitive detector for the measuring of translations of the darkenings in the penetrating radiation.

Translation is a vector characterized by a direction and magnitude. A position-sensitive detector 42 combined with a computer 43 as it is shown in FIG. 8 can separately measure the direction and the magnitude of the translation of penetrating radiation darkenings. This combination can function as detector 5 in FIG. 1. Position-sensitive detector 42 contains a plurality of sections 44 which are electrically connected to computer 43. The penetrating radiation strikes the surface of position-sensitive detector 42 in the form of shaped beams (a projection of aperture 12 through spatial filter 14, see FIG. 2). An output signal from each section 44 of detector 42 carries information about the distribution of the penetrating radiation sensed by detector 42. In a calibration measurement, computer 43 stores output signals that detector 42 produced in the presence of a reference object or in the absence of any object. A measurement is taken in the presence of object 4. The results of the two measurements are compared, and the magnitude and the direction of the translation of the penetrating radiation flow that passed through each zone of the object under investigation are determined. Computer 43 forms a projection 45 of object 4 by subtracting the calibration measurement from the actual measurement. The contrast and shape of regions in projection 45 indicate the magnitude and direction of the deviation of the penetrating radiation.

Figure 9:
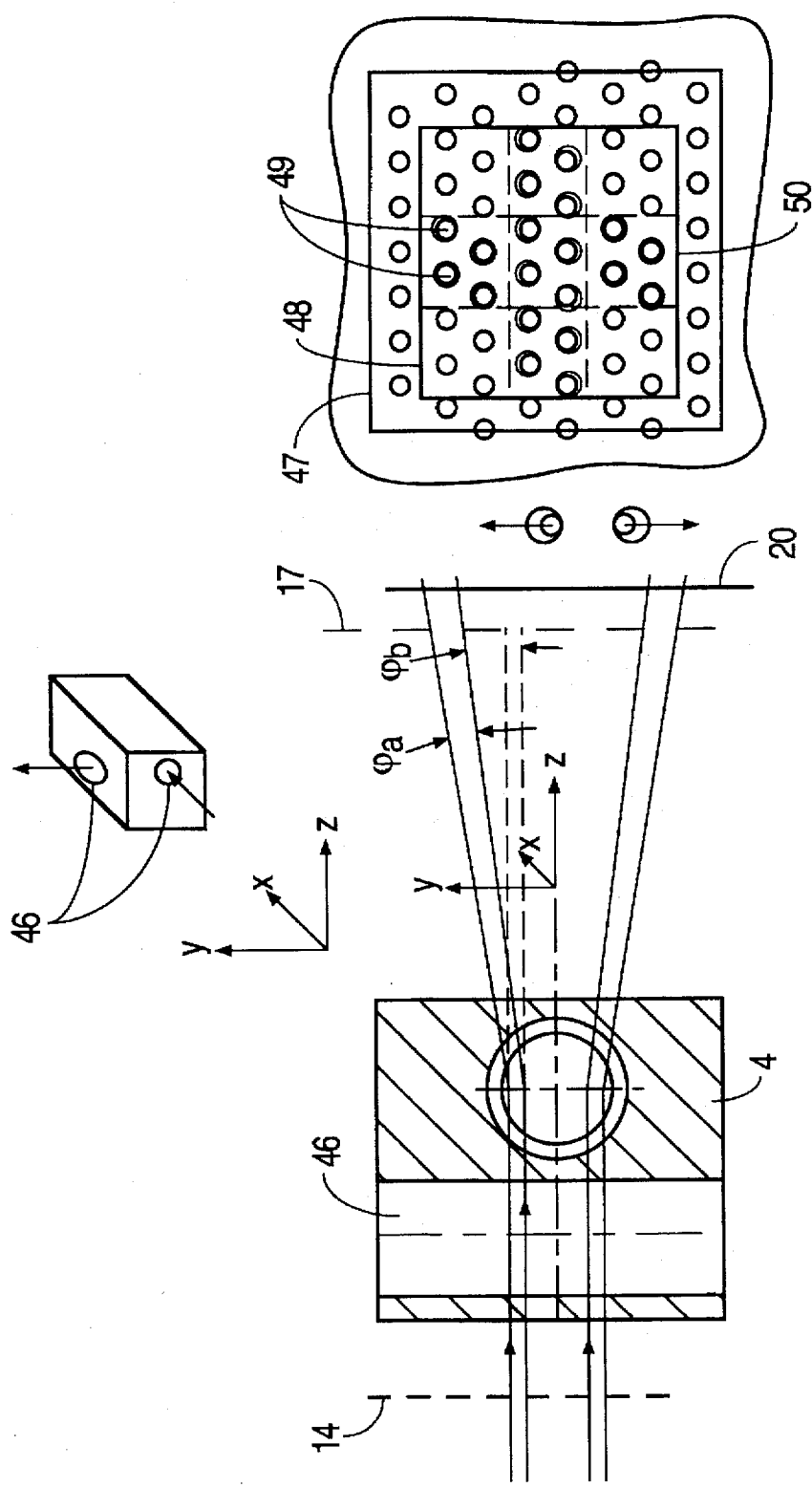
FIG. 9 illustrates a process for forming of a projection of an object.

FIG. 9 shows an imaging system forming a projection of an object 4 which is a paraffin cube with sides 20 mm in length and two bores 46 perpendicular to each other through the cube. Each of bores 46 is of 2 mm in diameter. Object 4 is located near spatial filter 14 in the path of a penetrating radiation beam which is a modulated X-ray beam. X-ray sensitive film 20 is close behind spatial filter 17 and acts as a detector. A photograph 47 formed on film 20 shows a projection 48 of object 4. Projection 48 includes a plurality of spots 49 formed by the rays that have passed through spatial filter 14 and been partly blocked by spatial filter 17.

Typically, spots 49 are on a background a produced by diffuse scattered X-rays. The background of projection 48 of object 4 appears as a dark square 50 with sides 40 mm in length and crossed lighter strips of 4 mm width which correspond with the projections of bores 46. The strips result because rays that cross bores 46 are attenuated less by 18 mm of paraffin than the rays that travel through 20 mm of paraffin. In projection 48, this is seen as the lesser darkening of the film emulsion.

Rays passing through bores 46 of object 4 in the direction perpendicular to bores 46 are deviated, in accordance with the lens law, to an angle proportional to the distance between the ray and the axis of the bore 46. Maximum angle of deviation for X-rays is about $2*10^{-5}$ radians or about 4 angular seconds. The deviated ray, after it has covered 1 m distance from spatial filter 17 to film 20 acquires a lateral displacement of about 0 to 0.02 mm. About twenty rays crossing bore 46 in each of its radial sections approach film 20 partly intercepted by spatial filter 17. Spatial filter 17 intercepts about 70% of each ray having maximum deflection and 100% of each ray that passes through the axis of apertures 46 without any deviation from their initial direction.

The cross-sectional area of all the apertures in spatial filter 14 provides radiation that covers about 15% of the total cross sectional area of object 4. Accordingly, not all areas of object 4 are projected to the detector (film 20). To increase the amount of information that can be extracted from photograph 47, object 4 can be displaced a distance X which ranges up to 0.01 mm into two directions with film 20 simultaneously displaced a distance 2*X in the same direction. Once displaced, areas of object 4 which were not irradiated previously by X-rays are photographed using film 20.

Although the present invention has been described with reference to particular embodiments, the description is only an example of the invention's application and should not be taken as a limitation. Various adaptations and combinations of features of the embodiments disclosed are within the scope of the present invention as defined by the following claims.

We claim:

1. A method of forming a projection indicating internal structure in an object, the method comprising:

modulating a flow of a penetrating radiation so that the flow contains separated beams;

directing the flow at the object so that at least a first portion of the flow passes through the object;

spatially filtering the first portion of the flow to remove penetrating radiation that passes through the object without being deflected, wherein the spatial filtering transmits a second portion of the flow;

detecting a deflection for each of the beams in the second portion of the flow; and forming a projection of the object from the second portion of the penetrating radiation, wherein contrast in the projection indicates differences in the deflections.

2. The method of claim 1, wherein modulating the flow comprises spatially filtering the penetrating radiation to block a portion of the penetrating radiation and pass a portion of radiation which forms the beams.

3. A method of forming a projection of an object, the method comprising:

modulating a flow of penetrating radiation so that the flow contains separated beams;

directing the flow at the object so that at least a portion of the flow passes through and then exits the object;

placing a screen in a path of the portion of the flow that exits the object, wherein the screen comprises: a plurality of first areas, each first area being positioned in a non-deflected path of an associated beam in the flow; and a plurality of second areas, each second area being outside the non-deflected path of an associated beam in the flow, wherein the first areas interact with the radiation in a manner that differs from a manner in which the second areas interact with the radiation;

detecting a deflection for each of the beams from interactions of the second areas with radiation deflected by the object; and forming a projection of the object using the detected interaction of the second areas with the radiation, wherein contrast in the projection indicates differences in the deflections of the beams.

4. The method of claim 3, wherein modulating the flow comprises spatially filtering penetrating radiation to block a portion of the penetrating radiation and transmit a portion of the penetrating radiation that forms the beams in the flow.

5. The method of claim 3, wherein the second areas interact with the penetrating radiation by converting the penetrating radiation into light, and detecting the deflections comprises detecting light from the second areas.

6. A method of forming a projection of an object, the method comprising:

modulating a flow of penetrating radiation so that the flow contains irregularities;

directing the flow at the object so that at least a portion of the flow passes through and then exits the object;

placing a screen in a path of the portion of the flow that exits the object, wherein the screen has a first area positioned in a non-deflected path of an irregularity in the flow and a second area that is outside non-deflected paths of the irregularities in the flow, wherein the first area of the screen converts penetrating radiation into light having a first characteristic and the second area converts penetrating radiation into light having a second characteristic which differs from the first characteristic;

detecting interactions of the second area with radiation deflected in the object by detecting light having the first characteristic; and forming the projection of the object according to the detected interactions of the second area with the radiation.

7. The method of claim 6, wherein the first characteristic is a first wavelength, and the second characteristic is a second wavelength that differs from the first wavelength.

8. The method of claim 7, wherein forming the projection comprises generating a color that result when a first of the irregularities in the penetrating radiation is deflected to strike portions of the first and second areas, the color depending on the relative proportions of light of the first wavelength and light of the second wavelength and indicating the deflection of the irregularity.

9. The method of claim 6, wherein the first characteristic is a first polarization and the second characteristic is a second polarization that differs from the first polarization.

10. A method of forming a projection of an object, the method comprising:

modulating a flow of penetrating radiation so that the flow contains irregularities;

determining a reference pattern indicating the relative positions of the irregularities when the object is outside the flow;

placing the object in the flow, wherein at least a portion of the flow passes through the object and forms a second pattern indicating the relative positions of the irregularities when the object is in the flow; and forming the projection for the object from a difference between the second pattern and the reference pattern.

11. The method of claim 10, wherein determining the reference pattern comprises:

placing a luminescent screen in the path of the flow of penetrating radiation when the object is outside the flow;

placing film in the path of light from the luminescent screen, wherein the light makes exposed regions of the film opaque; and forming a spatial filter from the exposed film.

12. The method of claim 11, wherein forming the projection comprises:

placing the luminescent screen in a path of penetrating radiation that exits the object;

placing the spatial filter in the path of light from the luminescent screen, wherein the spatial filter blocks light at positions of high intensity in the reference pattern; and forming a projection of the object using the light not blocked by the spatial filter.

13. An imaging system comprising:

a source of penetrating radiation;

a modulator positioned to create a plurality of separated beams in a flow of penetrating radiation from the source of penetrating radiation;

a spatial filter having areas opaque to the penetrating radiation, wherein each opaque area is positioned along a non-deflected path of an associated one of the beams; and a detector positioned to detect penetrating radiation that passes the spatial filter, wherein the detector detects a deflection for each of the beams.

14. The imaging system of claim 13, wherein the detector forms a projection of an object such that contrast in the projection depends on differences among the deflections and of the beams in the object.

15. An imaging system comprising:

a source of penetrating radiation;

a modulator positioned to create spatial irregularities in penetrating radiation from the source of penetrating radiation; and a luminescent screen having first areas positioned along non-deflected paths of the spatial irregularities, and second areas positioned outside the non-deflected paths of the radiation, wherein a luminescent property of the first areas differ from a corresponding luminescent property of the second areas.

16. The imaging system of claim 15, wherein the first areas luminesce to provide light having a first wavelength and the second areas luminesce to provide light having a second wavelength.

17. The imaging system of claim 16, further comprising a detector which generates a projection having contrast that indicates a difference between an intensity of light having the first wavelength and an intensity of light having the second wavelength.

18. The imaging system of claim 15, wherein the luminescence of first areas differs in intensity from the luminescence of the second areas.

19. The imaging system of claim 18, wherein the equal amounts of penetrating radiation in the first areas and second areas cause a lower luminescence from the first areas.

20. The imaging system of claim 15, further comprising a detector positioned to detect light from the second areas of the luminescent screen.

* * * * *